US006893996B2

United States Patent
Chu et al.

(10) Patent No.: US 6,893,996 B2
(45) Date of Patent: May 17, 2005

(54) PROCESS FOR THE PREPARATION OF A NICKEL/PHOSPHOROUS LIGAND CATALYST FOR OLEFIN HYDROCYANATION

(75) Inventors: Luis A. Chu, Forsyth, IL (US); Lucy M. Clarkson, Kennett Square, PA (US); Norman Herron, Newark, DE (US); Ronald J. McKinney, Wilmington, DE (US); Kenneth G. Moloy, Hockessin, DE (US); Zeru Tekie, Beaumont, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 348 days.

(21) Appl. No.: 09/994,102

(22) Filed: Nov. 26, 2001

(65) Prior Publication Data

US 2003/0100442 A1 May 29, 2003

(51) Int. Cl.$^7$ .......................... B01J 31/00; B01J 27/185
(52) U.S. Cl. ..................... 502/167; 502/167; 502/169; 502/213
(58) Field of Search ................................ 502/162, 167, 502/169, 213

(56) References Cited

U.S. PATENT DOCUMENTS

| | | |
|---|---|---|
| 3,631,191 A | 12/1971 | Kane et al. |
| 3,846,461 A | 11/1974 | Shook, Jr. |
| 3,847,959 A | 11/1974 | Shook, Jr. et al. |
| 5,061,669 A | 10/1991 | Puckette |
| 5,510,470 A | 4/1996 | Casalnuovo et al. |
| 5,512,695 A | 4/1996 | Kreutzer et al. |
| 5,512,696 A | 4/1996 | Kreutzer et al. |
| 5,523,452 A | 6/1996 | Kricsfalussy et al. |
| 5,523,453 A | 6/1996 | Breikss |
| 5,663,369 A | 9/1997 | Kreutzer et al. |
| 5,693,843 A | 12/1997 | Breikss et al. |
| 5,723,641 A | 3/1998 | Tam et al. |

OTHER PUBLICATIONS

Katayama Eiji, "Method of preparing nickel chloride anhydride", JP 2002 274854, Sep. 25, 2002, vol. 2003, No. 1, abstract—& DATABASE WPI week 200318, Derwent Pub. Ltd., London, GB; AN 2003–178451, XP002245933, JP 2002–274845 A, abstract.

Ishiyama Naoki, "Production of anhydrous nickel chloride", JP 11 263625 A (Sumitomo Metal Mining Co. Ltd.), vol. 1999, No. 14, Sep. 28, 1999 abstract—& WPI week 199952, Derwent Pub. Ltd., London, GB; AN 1999–604817, XP002245934 & JP 11 263625 A abstract.

Kanichev R N et al., Anhydrous nickel chloride prepn.—by heating and subliming the hexa–hydrate in inert gas atoms, Database WPI, week 198501, Derwent Pub. Ltd., London, GB; AN 1985–005455, XP002245935—& SU 1 096 223 A (Leningrad Lensovet Tech), Jun. 7, 1984 abstract (translation).

Nishino, Kenji et al., "Anhydrous nickel chloride", Toray Industries, Inc., Database CA, Chemical Abstracts Service, Columbus OH, DATABASE accession No. 75:65720, XP002245931 abstract, Feb. 3, 1971 & JP 46 004446 B abstract.

Tayim, H. A. et al., "Dehydration of nickel (II) chloride hexadydrate", Database CA, Chemical Abstracts Service, Columbus OH, DATABASE accession No. 73:72600, XP002245932 abstract & Chemistry & Industry (London, UK) (1970) No. 28,919.

Copy of the International Search Report for PCT/US 02/36468, dated Jul. 16, 2003.

Banse, Hildegard et al. "Gmelins Handbuch der Anorganischen Chemie" 1996, Verlag Chemie, Weinheim Germany, XP002239171, "Nickel" (System–No. 57, Part B—Delivery 2) p. 538 (Translation).

Communication Relating to the Results of the Partial International Search Report for PCT/US 02/36468.

*Primary Examiner*—Mark L. Bell
*Assistant Examiner*—J. Pasterczyk

(57) ABSTRACT

A process for preparing a hydrocyanation catalyst comprising contacting a bidentate phosphorous-containing ligand with a molar excess of nickel chloride in the presence of a nitrile solvent and a reducing metal which is more electropositive than nickel. Preferably, the nickel chloride is dried before use.

18 Claims, No Drawings

PROCESS FOR THE PREPARATION OF A NICKEL/PHOSPHOROUS LIGAND CATALYST FOR OLEFIN HYDROCYANATION

FIELD OF THE INVENTION

This invention relates to a process for the preparation of a hydrocyanation catalyst which is a complex of nickel and a bidentate phosphorous compound.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phoshite and phosphinite ligands can be used to form nickel-based catalysts to perform such hydrocyanation reactions.

U.S. Pat. No. 3,903,120 discloses a process for preparing zerovalent nickel complexes by reacting elemental nickel with a monodentate phosphorous ligand of the formula $PZ_3$ where Z is an alkyl or alkoxy group, preferably an aryloxy group. The process uses finely divided elemental nickel and is preferably carried out in the presence of a nitrile solvent. The reaction is taught to be carried out in the presence of excess ligand.

U.S. Pat. No. 3,846,461 discloses a process for preparing zerovalent nickel complexes of triorganophosphites by reacting triorganophosphite compounds with nickel chloride in the presence of a finely divided reducing metal which is more electropositive than nickel, and in the presence of a promoter selected from the group consisting of $NH_3$, $NH_4X$, $Zn(NH_3)_2X_2$, and mixtures of $NH_4X$ and $ZnX_2$, where X is a halide. Reducing metals include Na, Li, Mg, Ca, Ba, Sr, Ti, V, Fe, Co, Cu, Zn, Cd, Al, Ga, In, Sn, Pb, and Th, with Zn being preferred.

U.S. Pat. No. 5,523,453 discloses a method of preparing nickel hydrocyanation catalysts containing bidentate phosphorous ligands. Zero-valent nickel compounds that contain ligands that can be displaced by the bidentate phosphorous ligand are a preferred source of nickel. Two such compounds are $Ni(COD)_2$, where COD is 1,5-cyclooctadiene, and $(oTTP)_2Ni(C_2H_4)$, where OTTP is $P(O\text{-ortho-}C_6H_4CH_3)_3$. Alternatively, divalent nickel compounds may be combined with reducing agents to produce a suitable nickel source. In the latter method of preparing catalyst, as the temperature of the catalyst preparation increases, the catalyst formation rate increases, but the amount of degradation product also increases. Accordingly, there is a need in the art for a process that allows for high reaction rates and low degradation.

SUMMARY OF THE INVENTION

The present invention is a process for preparing a hydrocyanation catalyst by contacting a bidentate phosphorus-containing ligand with nickel chloride in the presence of a nitrile solvent and a reducing metal which is more electropositive than nickel, the nickel chloride being in molar excess with respect to the reducing metal.

DETAILED DESCRIPTION OF THE INVENTION

The catalysts of the present invention may be prepared by contacting nickel chloride with a bidentate phosphorous-containing ligand in the presence of a reducing metal, the nickel chloride being in molar excess with respect to the reducing metal. The reducing metal can be any metal which is more electropositive than nickel. Such metals include Na, Li, K, Mg, Ca, Ba, Sr, Ti, V, Fe, Co, Cu, Zn, Cd, Al, Ga, In, Sn, Pb, and Th. Most preferred are Fe and Zn. The reducing metal (hereinafter "MET") is preferably finely-divided. The expression "finely-divided" means that the metal is of a particle size of less than 20 mesh.

Surprisingly, the rate of reaction is substantially independent of the concentration of the phosphorus-containing ligand or the amount of reducing metal, but, rather, depends on the amount of $NiCl_2$ present and the reaction temperature. Accordingly, increasing the amount of $NiCl_2$ increases the reaction rate. Since undesirable side reactions, especially degradation, increase with temperature, using excess nickel chloride to increase the catalyst formation rate may allow a decrease in reaction temperature which will decrease undesirable side reactions. The reaction is usually carried out such that the reducing metal is the limiting reagent. In other words, the amount of the $NiCl_2$ converted to catalyst is controlled by the amount of reducing metal added.

The source of nickel for this invention is preferably nickel (II) chloride, $NiCl_2$. Either hydrated or anhydrous forms of $NiCl_2$ may be used. Anhydrous $NiCl_2$ is preferred in order to minimize the hydrolytic degradation of the ligand. The expression "anhydrous" means that the nickel chloride contains less than 2% by weight water. Nickel chloride containing 1% or less water is preferred. Anhydrous nickel chloride may be obtained by heating hydrated forms of $NiCl_2$ to temperatures of about 200° C. to about 240° C. Heating the $NiCl_2$ above about 240° C. produces $NlCl_2$ that is less reactive in the catalyst preparation and is not preferred. Also, heating the $NiCl_2$ for an extended period of time will also produce lower reactivity product. Accordingly, the $NiCl_2$ should not be heated above about 200° C. for more than about 12 hours.

The expression "hydrated $NiCl_2$" means $NiCl_2$ containing 2% or more water by weight. Examples of hydrated $NiCl_2$ include the dihydrate, the hexahydrate and aqueous solutions of $NiCl_2$. Preferred sources for producing anhydrous $NiCl_2$ are the hexahydrate product and an aqueous solution. $NiCl_2$ as an aqueous solution is particularly preferred. The aqueous solution is available commercially as an approximately 29 weight percent $NiCl_2$ aqueous solution. However, it is believed that the invention is not limited to this weight percentage and aqueous solutions with different weight percent $NiCl_2$ will work. For practical reasons, the preferred aqueous solution contains 20 to 31 weight percent $NiCl_2$. The lower limit is due to cost effectiveness of dehydrating a dilute solution. The upper limit is due to $NiCl_2$ solubility at ambient temperature, particularly due to the precipitation of $NiCl_2(H_2O)_6$.

A preferred method of drying hydrated $NiCl_2$ is to first dry the $NiCl_2$ by spray or flash drying and then further dry the resulting product by thermal drying. A number of types of spray or thermal dryers are known to one skilled in the art. Pneumatic conveying dryers and flash dryers are known to be interchangeable terminology in the drying trade. The choice of which type to use is not critical. Examples of spray dryers are co-current flow, counter current, and mixed flow. In this preferred process, the spray dryer should have an exit temperature of 120 to 150° C., preferably 130 to 135° C. Mean residence time of heat exposure with the spray dryer should be 1 to 75 seconds, preferably 1 to 45 seconds. The resulting product is typically the dihydrate product which contains approximately 22 weight percent water.

Following spray or flash drying, the product is preferably further dried by thermal drying. Choice of dryer type is not critical. The thermal drying may be by direct or indirect drying in which the heat is primarily by conduction or convection. Thermal drying may occur under reduced pressure or with a dry inert gas flow. For economic reasons, the dry inert gas is preferably nitrogen. Thermal drying should occur at a temperature between about 200 and about 240° C. The time of drying should not exceed about 12 hours.

The catalyst formation reaction is carried out in the presence of a nitrile solvent, preferably 3-pentenenitrile or 2-methyl-butenenitrile. The concentration of ligand may range from about 1% to 90% by weight. For practical reasons the preferred range of ligand concentration is 5% to 50%. The amount of reducing metal (MET) is determined by the desired nickel catalyst product concentration. The preferred amount of reducing metal (MET) will generally fall in the range of 0.1% to 5% of the reaction mass. The amount of $NiCl_2$ will be in molar excess to the reducing metal. The molar ratio of $NiCl_2$ to MET ranges from 1.1:1 to 100:1. The preferred ratio of $NiCl_2$:MET ranges from 2:1 to 50:1. The reaction temperature may range from 0° C. to 120° C. The preferred temperature range is dependent on the $NiCl_2$ form. Hydrated forms of $NiCl_2$ react rapidly at lower temperatures than anhydrous $NiCl_2$. For $NiCl_2.2H_2O$, the preferred temperature range is 0° C. to 60° C., and the most preferred range is 25° C. to 50° C. For anhydrous $NiCl_2$, the preferred temperature range is 30° C. to 100° C., and the most preferred range is 50° C. to 90° C. The reaction may be run within a wide pressure range. For practical reasons, the preferred pressure ranges from about 5 psia to 50 psia (34 to 340 kPa). The reaction may be run in batch or continuous mode.

Suitable ligands for the present invention are bidentate phosphorous-containing ligands selected from the group consisting of bidontate phosphites, bidentate phosphinites, and bidentate phosphines. Most preferred ligands are bidentate phosphite ligands.

The most preferred bidentate phosphite ligands are of the following structural formulae:

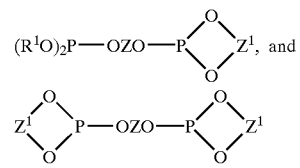

In these formulae, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the groups consisting of structural formulae I, II, III, and IV:

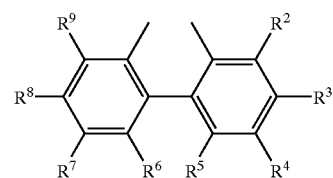

I wherein:

$R^2$ and $R^9$ are the same and are selected from H, $C_1$ to $C_{12}$ alkyl, and $C_1$ to $C_{12}$ alkoxy;

$R^3$ and $R^8$ are the same and are selected from H, $C_1$ to $C_{12}$ alkyl, and $C_1$ to $C_{12}$ alkoxy;

$R^4$ and $R^7$ are the same and are selected from H, $C_1$ to $C_{12}$ alkyl, and $C_1$ to $C_{12}$ alkoxy;

$R^5$ and $R^6$ are the same and are selected from H, $C_1$ to $C_{12}$ alkyl, and $C_1$ to $C_{12}$ alkoxy;

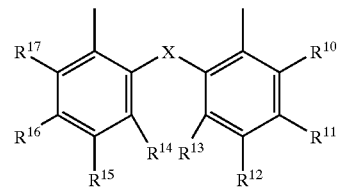

II wherein:

X is O, S, or $CH(R^{18})$;

$R^{10}$ and $R^{17}$ are the same and are selected from H, $C_1$ to $C_{12}$ alkyl, and $C_1$ to $C_{12}$ alkoxy;

$R^{11}$ and $R^{16}$ are the same and are selected from H, $C_1$ to $C_{12}$ alkyl, and $C_1$ to $C_{12}$ alkoxy;

$R^{12}$ and $R^{15}$ are the same and are selected from H, $C_1$ to $C_{12}$ alkyl, and $C_1$ to $C_{12}$ alkoxy;

$R^{13}$ and $R^{14}$ are the same and are selected from H, $C_1$ to $C_{12}$ alkyl, and $C_1$ to $C_{12}$ alkoxy; and $R^{18}$ is H or $C_1$ to $C_{12}$ alkyl;

III

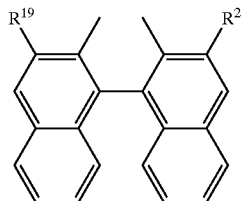

wherein:

$R^{19}$ and $R^{20}$ are the same and are selected from H, $C_1$ to $C_{12}$ alkyl, and $C_1$ to $C_{12}$ alkoxy; and $CO_2R^{21}$, $R^{21}$ is $C_1$ to $C_{12}$ alkyl or $C_6$ to $C_{10}$ aryl, unsubstituted or substituted with $C_1$ to $C_4$ alkyl groups. The aryl groups are preferably phenyl or naphthyl.

IV

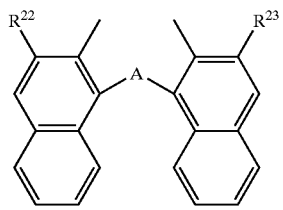

wherein:

A is O, S, $CH(R^{24})$;

$R^{22}$ and $R^{23}$ are the same and are selected from H and $CO_2R^{25}$;

$R^{24}$ is H or $C_1$ to $C_{12}$ alkyl; and $R^{25}$ is $C_1$ to $C_{12}$ alkyl.

In the above structural formulae, the $C_1$ to $C_{12}$ alkyl, and $C_1$ to $C_{12}$ alkoxy groups may be straight chains or branched.

Examples of diorganophosphite compounds that can be made by the present process include those having the formulae V to XXVI, shown below.

V

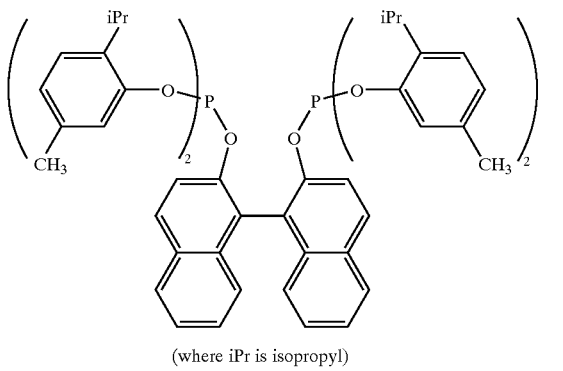

(where iPr is isopropyl)

VI

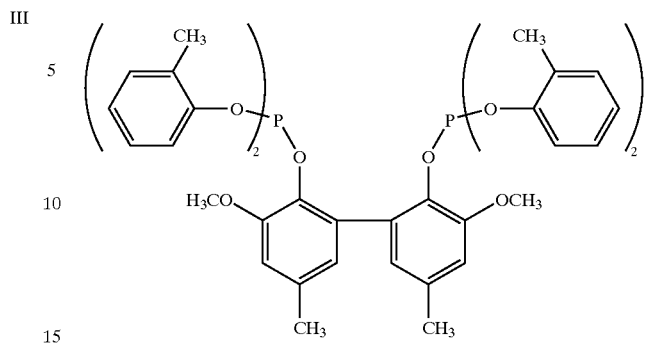

VII

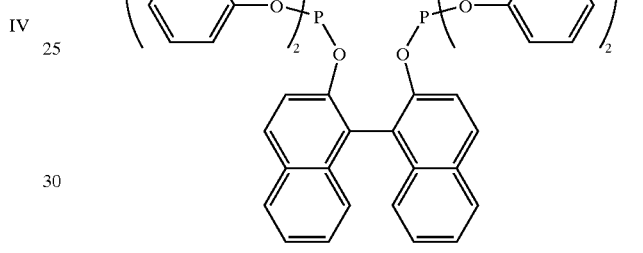

(where iPr is isopropyl)

VIII

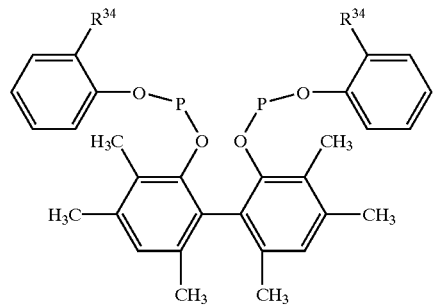

(where $R^{34}$ is methyl or ethyl)

IX

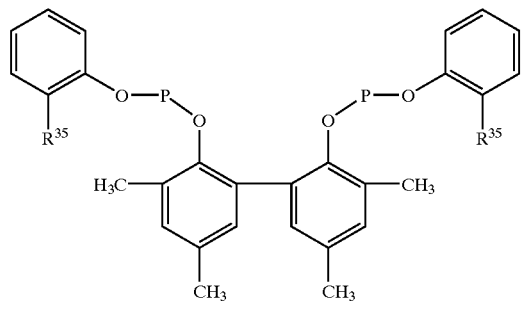

(where $R^{35}$ is methyl, ethyl, or isopropyl)

X
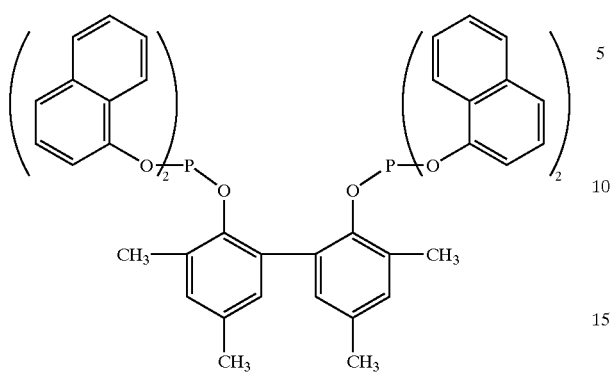
XI
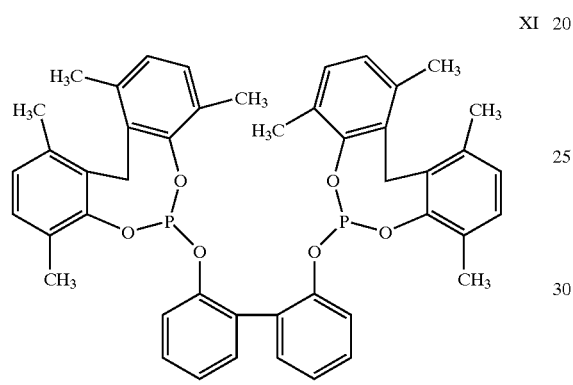
XII
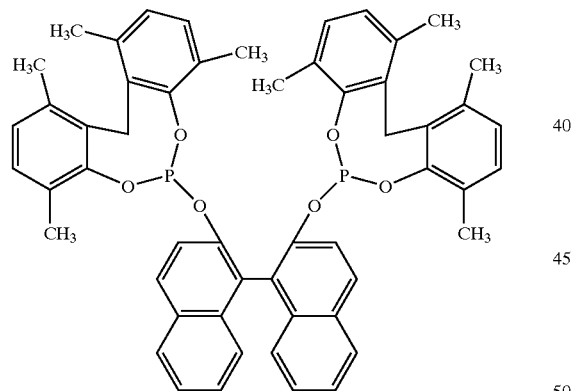
XIII
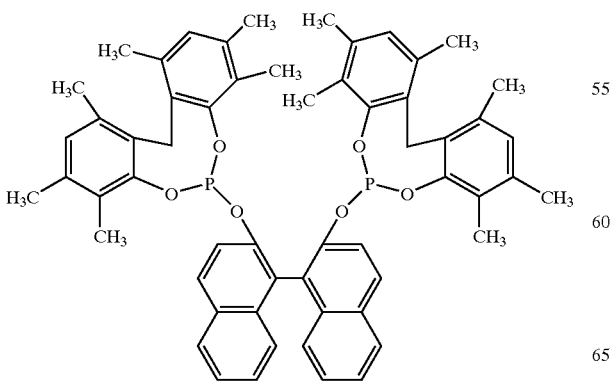
XIV
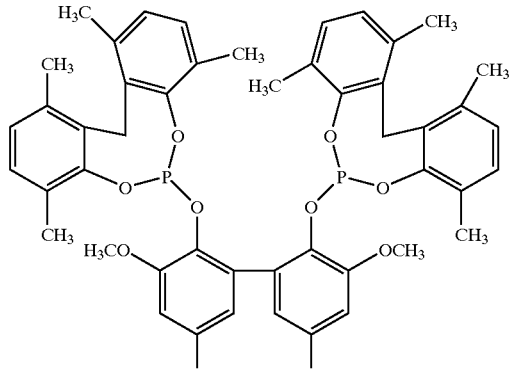
XV
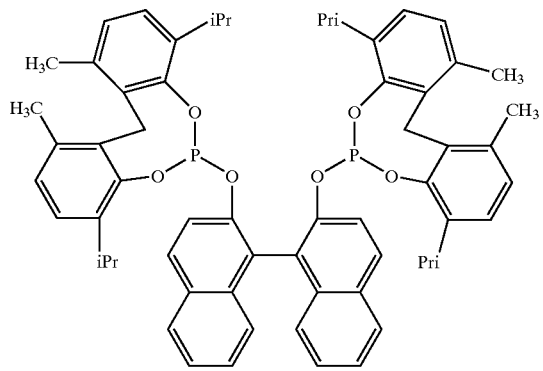
(where iPr is isopropyl)
XVI
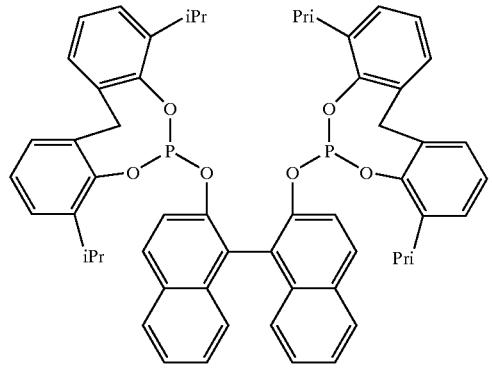
(where iPr is isopropyl)
XVII
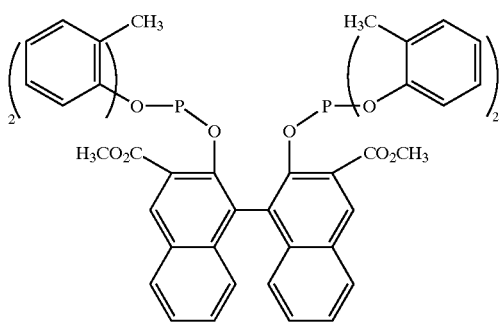

XVIII
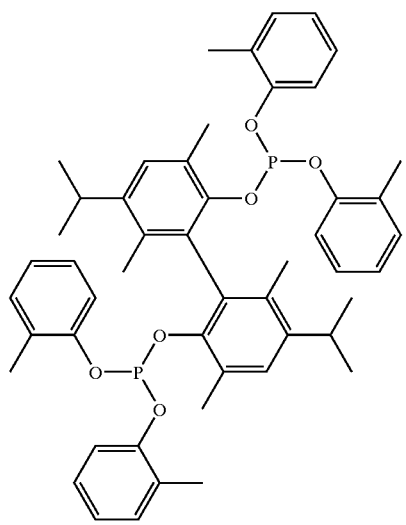
XXI
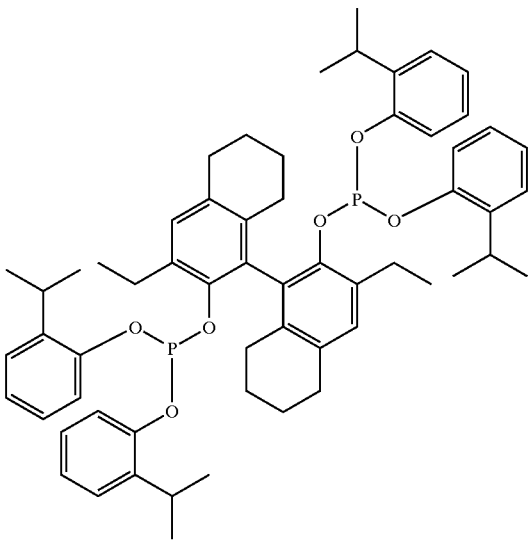
XIX
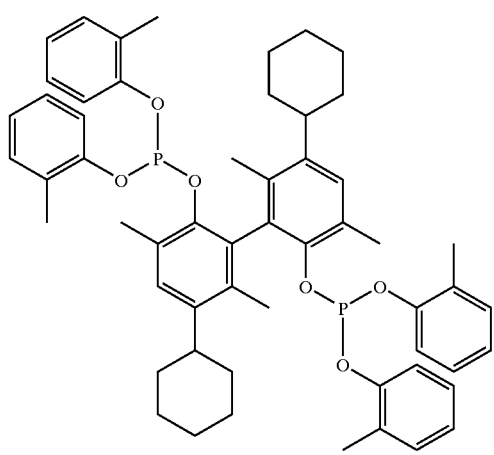
XII
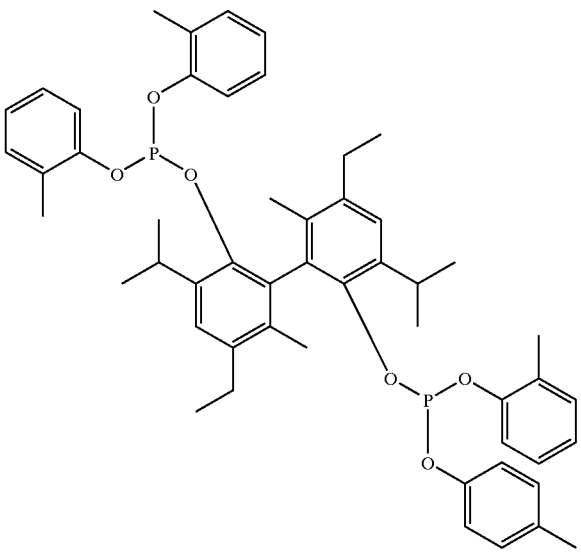
XX
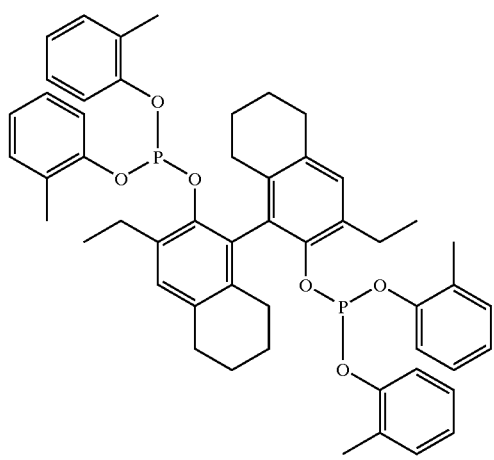
XXIII
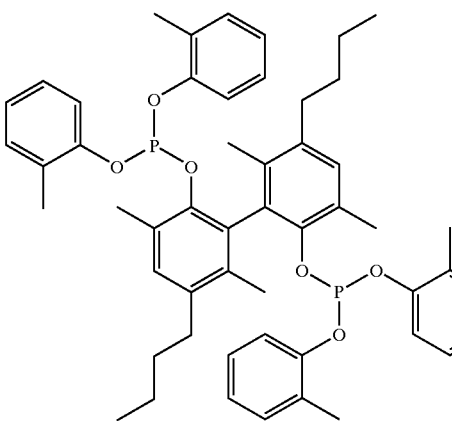

-continued

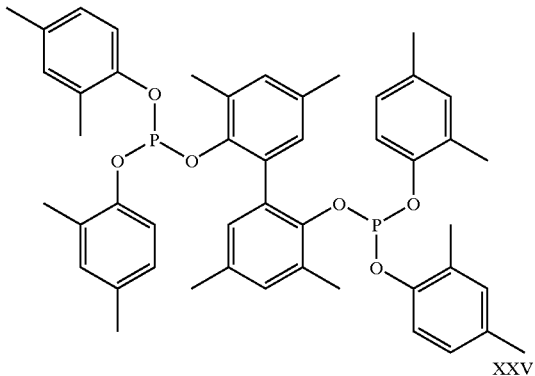

XXIV

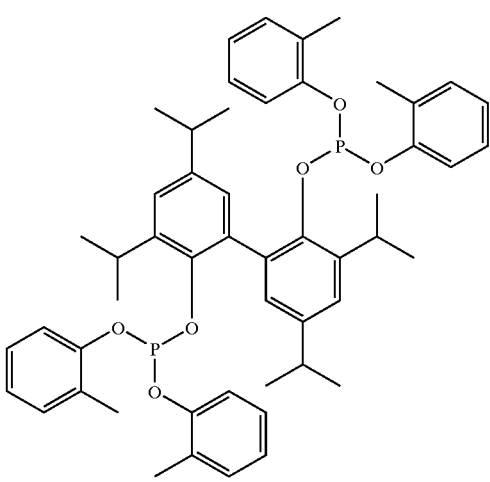

XXV

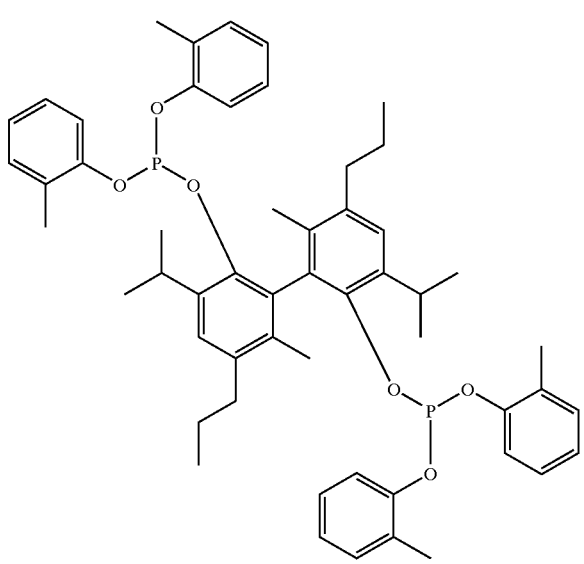

XXVI

Suitable bidentate phosphites are of the type disclosed in U.S. Pat. Nos. 5,512,695, 5,512,696, 5,663,369, and 5,723,641, the disclosures of which are incorporated herein by reference. Suitable bidentate phosphinites are of the type disclosed in U.S. Pat. Nos. 5,523,453 and 5,693,843, the disclosures of which are incorporated herein by reference.

The reaction may be carried out in a manner such that unreacted excess $NiCl_2$ may be separated from the reaction product by filtration or centrifugation. The collected excess nickel chloride can then be recycled back to a catalyst preparation reactor.

EXAMPLES

The invention is illustrated by the following non-limiting examples. In the following examples, the reducing metal is the limiting reagent in each reaction and therefore the extent of reaction (conversion) is expressed as the percentage of the reducing metal reacted. Unless otherwise noted, the extent of reaction (conversion) is determined by analyzing for the amount of active nickel produced by the catalyst synthesis reaction. The analysis is carried out by treating a solids-free aliquot of the reaction solution with dimethyl acetylenedicarboxylate (DMAD), which forms a stable nickel complex, (Ligand)Ni(DMAD), and analyzing quantitatively for this complex by High Pressure Liquid Chromatography (HPLC).

Examples 1–6, and 11–18 utilize anhydrous $NiCl_2$ as produced in Example 20. $NiCl_2.2H_2O$ utilized in Examples 7–10 was produced by heating nickel chloride hexahydrate to about 130° C. under reduced pressure.

Examples 1–6 illustrate that the catalyst synthesis reaction rate depends on the amount of anhydrous $NiCl_2$ charged to the reaction.

Example 1

A 100 mL reaction vessel fitted with a mechanical stirrer was charged under a nitrogen atmosphere blanket with 3-pentenenitrile (80 mL; 830 mmol), ligand V (18 g; 19 mmol), $NiCl_2$ (3.22 g; 24.8 mmol), and zinc powder (0.61 g; 9.3 mmol). The reaction mixture was stirred at 100° C. for 3 hours, and samples were withdrawn every 30 minutes for analysis. After 2 hours, 70% conversion of $NiCl_2$ to catalyst had occurred, and after 3 hours, greater than 95% conversion of $NiCl_2$ to catalyst had occurred.

Example 2

A reaction was executed in the manner of example 1, except that the amount of $NiCl_2$ charged (1.61 g; 12.4 mmol) was half as much. After 2 hours, about 37% conversion of $NiCl_2$ to catalyst had occurred, and after 3 hours, about 60% conversion of $NiCl_2$ to catalyst had occurred.

In the following examples 3 to 10, a catalyst source which was depleted in active nickel, called "recycle catalyst," was recharged. In these cases, "recycle catalyst" contained 11 weight percent (wt %) Ligand V in 3-pentenenitrile.

Example 3

A 100 mL reaction vessel fitted with a mechanical stirrer was charged under a nitrogen atmosphere blanket with recycle catalyst (100 g, containing 11 wt % ligand V), $NiCl_2$ (1.21 g; 9.3 mmol), and zinc powder (0.61 g; 9.3 mmol). The reaction mixture was stirred at 80° C. for 4 hours, and samples were withdrawn every 30 minutes for analysis. After 4 hours, less than 2% conversion $NiCl_2$ to catalyst had occurred.

Example 4

A reaction was executed in the manner of example 3, except that the amount of $NiCl_2$ charged (2.42 g; 18.6 mmol)

was twice as much as in example 3. After 4 hours, 35% conversion of $NiCl_2$ to catalyst had occurred.

Example 5

A reaction was executed in the manner of example 3, except that the amount of $NiCl_2$ charged (4.84 g; 37.2 mmol) was four times as much as in example 3. After 4 hours, 75% conversion of $NiCl_2$ to catalyst had occurred.

Example 6

A reaction was executed in the manner of example 3, except that the amount of $NiCl_2$ charged (7.26 g; 56.0 mmol) was six times as much as in example 3. After 2 hours, 77% conversion of $NiCl_2$ to catalyst had occurred, and after 4 hours, 83% conversion of $NiCl_2$ to catalyst had occurred.

The following examples 7 to 10 show that the use of hydrated $NiCl_2$ ($NiCl_2.2H_2O$) produces the same rate dependence on nickel chloride concentration as anhydrous $NiCl_2$, but at a lower temperature.

Example 7

A 100 mL reaction vessel fitted with a mechanical stirrer was charged under a nitrogen atmosphere blanket with recycle catalyst (100 g, containing 11 wt % ligand V), $NiCl_2.2H_2O$ (1.21 g; 7.3 mmol), and zinc powder (0.61 g; 9.3 mmol). The reaction mixture was stirred at 25° C. for 4 hours, and samples were withdrawn every 30 minutes for analysis. After 4 hours, about 13% conversion $NiCl_2$ to catalyst had occurred.

Example 8

A reaction was executed in the manner of example 7, except that the amount of $NiCl_2.2H_2O$ charged (2.42 g; 14.6 mmol) was twice as much as in example 7. After 4 hours, 27% conversion of $NiCl_2$ to catalyst had occurred.

Example 9

A reaction was executed in the manner of example 7, except that the amount of $NiCl_2.2H_2O$ charged (4.84 g; 29.2 mmol) was four times as much as in example 7. After 4 hours, 93% conversion of $NiCl_2$ to catalyst had occurred.

Example 10

A reaction was executed in the manner of example 7, except that the amount of $NiCl_2.2H_2O$ charged (7.26 g; 43.8 mmol) was six times as much as in example 7. After 30 minutes, greater than 95% conversion of $NiCl_2$ to catalyst had occurred.

Comparative Example 1 illustrates that increasing the molar ratio of the reducing metal relative to $NiCl_2$ does not increase the reaction rate. In this example, $NiCl_2$ is the limiting reagent, and the extent of reaction is reported as the conversion of $NiCl_2$. The $NiCl_2$ was that produced as in Example 20.

Comparative Example 1

A "recycle catalyst" solution (9 grams of 30 wt % Ligand V) was treated with $NiCl_2$ (0.11 grams) and zinc (0.10 g). The mixture was agitated and heated at about 100° C. Analysis of a clear-liquid sample after 2 hours revealed 54% conversion of the $NiCl_2$. Reactions executed in a similar manner, except that the zinc charged was 0.20 grams and 0.40 grams, resulted in conversions of 54% and 50%, respectively.

The following examples 11 to 17 show that the process of the present invention is applicable to additional phosphorous-containing ligands, and that the same effects are observed when iron is used as the reducing agent. In these examples, the extent of reaction was determined by measuring nickel in solution by Inductively Coupled Plasma (ICP).

Example 11

A solution of Ligand XXIV was prepared by dissolving 2.497 grams of Ligand XXIV in 24.008 grams of dry 3-pentenenitrile. An aliquot of this solution (13.0 grams) was mixed with anhydrous $NiCl_2$ (1.22 grams) and zinc (0.102 grams). The mixture was agitated and heated at a temperature of about 80° C. Analysis of a clear liquid-only sample taken after 2 hours revealed 56% conversion in a similar reaction, except that only 0.20 grams of $NiCl_2$ was charged to the mixture, only 10% conversion was found after 2 hours.

Example 12

A solution of Ligand XXI was prepared by dissolving 3.03 grams of Ligand XXI in 24.16 grams of dry 3-pentenenitrile. An aliquot of this solution (13.38 grams) was mixed with 1.20 grams of anhydrous $NiCl_2$ and 0.10 grams of zinc. The mixture was agitated and heated at a temperature of about 81° C. Analysis of a clear liquid-only sample taken after 2 hours revealed 41% conversion. In a similar reaction, except that only 0.20 grams of $NiCl_2$ was charged to the mixture, only 10% conversion was found after 2 hours.

Example 13

A solution of Ligand XVIII was prepared by dissolving 2.59 grams of Ligand XVIII in 24.0 grams of dry 3-pentenenitrile. An aliquot of this solution (13.38 grams) was mixed with 1.20 grams of anhydrous $NiCl_2$ and 0.10 grams of zinc. The mixture was agitated and heated at a temperature of about 80° C. Analysis of a clear liquid-only sample taken after 2 hours revealed 73% conversion. In a similar reaction, except that only 0.20 grams of $NiCl_2$ was charged to the mixture, only 14% conversion was found after 2 hours.

Example 14

A solution of Ligand XIX was prepared by dissolving 2.85 grams of Ligand XIX in 24.0 grams of dry 3-pentenenitrile. An aliquot of this solution (13.4 grams) was mixed with 1.20 grams of anhydrous $NiCl_2$ and 0.10 grams of zinc. The mixture was agitated and heated at a temperature of about 78° C. Analysis of a clear liquid-only sample taken after 2 hours revealed 38% conversion. In a similar reaction, except that only 0.20 grams of $NiCl_2$ was charged to the mixture, only 10% conversion was found after 2 hours.

Example 15

A solution of Ligand XX was prepared by dissolving 2.67 grams of Ligand XX in 24.0 grams of dry 3-pentenenitrile. An aliquot of this solution (13.0 grams) was mixed with 1.23 grams of anhydrous $NiCl_2$ and 0.10 grams of zinc. The mixture was agitated and heated at a temperature of about 81° C. Analysis of a clear liquid-only sample taken after 2 hours revealed 59% conversion. In a similar reaction, except that only 0.20 grams of $NiCl_2$ was charged to the mixture, only 10% conversion was found after 2 hours.

Example 16

A solution of Ligand XXV was prepared by dissolving 2.68 grams of Ligand XXV in 24.0 grams of dry 3-pentenenitrile. An aliquot of this solution (13.1 grams) was mixed with 1.20 grams of anhydrous $NiCl_2$ and 0.10 grams of zinc. The mixture was agitated and heated at a temperature of about 81° C. Analysis of a clear liquid-only sample taken after 2 hours revealed 45% conversion. In a similar reaction, except that iron powder (0.43 grams) was charged to the mixture instead of zinc, 34% conversion was found after 2 hours.

Example 17

A solution of Ligand XXVI was prepared by dissolving 2.77 grams of Ligand XXVI in 24.0 grams of dry 3-pentenenitrile. An aliquot of this solution (12.6 grams) was mixed with 1.20 grams of anhydrous $NiCl_2$ and 0.10 grams of zinc. The mixture was agitated and heated at a temperature of about 80° C. Analysis of a clear liquid-only sample taken after 2 hours revealed 37% conversion. In a similar reaction, except that iron powder (0.42 grams) was charged to the mixture instead of zinc, 38% conversion was found after 2 hours.

Example 18

A solution of Ligand V was prepared by dissolving 3.03 grams of Ligand V in 24.0 grams of dry 3-pentenenitrile. An aliquot of this solution (13.3 grams) was mixed with 1.20 grams of anhydrous $NiCl_2$ and 0.44 grams of iron. The mixture was agitated and heated at a temperature of about 81° C. Analysis of a clear liquid-only sample taken after 2 hours revealed 16% conversion. In a similar reaction, except that only 0.2 grams of $NiCl_2$ was charged to the mixture, only 7% conversion was found after 2 hours.

Examples 19–24 demonstrate preferred methods of drying $NiCl_2$. Comparative Examples 2–3 are presented for comparison to the present invention and show that overheating while drying will lead to a less reactive material. "BET surface area" analysis refers to an analytical technique, well known to those skilled in the art, for measuring surface area of a solid material. The letters "BET" refer to Brunauer Emmett Teller, who developed the theory of multilayer gas adsorption/absorption onto solid surfaces. For example, using nitrogen gas at 77° K., the surface area of a solid material may be estimated by measuring the number of moles of nitrogen adsorbed as a function of the partial pressure of the gas for a given weight of solid. By applying the sorption theory of BET to the resulting isotherm absorption curve, it is easy to determine an effective surface area for the solid.

Example 19

10 g of nickel chloride hexahydrate was spread thinly in a clean quartz boat in a quartz-lined tube furnace equipped with a flow of 100 mL/min dry nitrogen. The exit nitrogen stream was passed through a mineral oil bubbler and vented to a hood. The sample was then heated to 240° C. over 15 minutes and held there for a total of 60 minutes. The sample was then cooled and sealed and taken into a nitrogen-flushed glove box for collection and storage prior to catalyst preparation experiments. A small portion of the material was analyzed for water content by Thermogravimetric Analysis (TGA) by heating it to 400° C. at 10° C./min. The weight loss at approximately 200° C. provided the measure of water in the sample.

This sample contained 0.3 weight percent water and had a BET surface area of 35 $m^2/g$ and an estimated crystallite size of 9 nm. When used in a catalyst preparation similar to that of Example 1, this material generated 76% conversion.

Comparative Example 2

The procedure of Experiment 19 was repeated, except that the nickel chloride was additionally heated to 350° C. for 30 minutes in nitrogen. The recovered sample had for less than 0.05 weight percent water, BET surface area of 13 $m^2/g$ and estimated crystallite size of 22 nm. When used in a catalyst preparation similar to that of Example 1, this material generated 36% conversion.

Comparative Example 3

The procedure of Experiment 19 was repeated, except that the nickel chloride was additionally heated to 500° C. for 30 minutes in nitrogen. The recovered sample had less than 0.05 weight percent water, BET surface area of 2 $m^2/g$ and estimated crystallite size of 44 nm. When used in a catalyst preparation similar to that of Example 1, this material generated 1% conversion.

Example 20

A 9.1 kg of $NiCl_2$ hydrate, containing 10.9 weight percent $H_2O$, was loaded into a rotary vacuum dryer. 20 kg of $NiCl_2$ hexahydrate was added to the dryer, resulting in an equivalent $NiCl_2$ charge containing 34.7 weight percent $H_2O$. The pressure in the dryer was reduced to 100 torr (690 kPa), and the temperature in the dryer was gradually increased to 100° C. over a 5 hour period. The expression "temperature in the dryer" refers to the temperature of the bulk contents. The vacuum dryer was indirectly heated with a hot oil supply at a temperature no higher than 20° C. higher than the measured bulk temperature. TGA tests confirmed that the dryer contents were dehydrated to a residual moisture of 21.5 weight percent $H_2O$, equivalent to a dihydrate state. The temperature in the dryer was then raised to 200° C. over a 4 hour period, and subsequently raised to 240° C. over a 2 hour period. TGA tests showed than the residual moisture was reduced to less than 0.1 weight percent $H_2O$. It had a BET surface area of 24 $m^2/g$ and had an estimated crystallite size of 17 nm. Approximately 17 kg of anhydrous $NiCl_2$ product was recovered. When used in a catalyst preparation similar to that of Example 1, this material generated 79% conversion.

Example 21

An aqueous solution containing approximately 29 weight percent $NiCl_2$ was pumped into a spray dryer at an average rate of 33.5 kg/hr. Filtered ambient air was indirectly heated to 400° C. and injected co-currently at an average rate of 327 kg/hr. Under these conditions, the average outlet temperature of the air exiting the spray dryer was 135° C. During a 4 hour tests, 50 kg of $NiCl_2$ dihydrate was produced containing about 22 weight percent $H_2O$.

About 30 kg of the spray dried product was loaded into the same rotary vacuum dryer as in Example 20. The pressure in the rotary dryer was reduced to 50 torr (345 kPa), and the temperature in the dryer was increased to 220° C. over a 2 hour period, and maintained for another 3 hours. TGA tests showed than the residual moisture was reduced to less than 0.1 weight percent $H_2O$, and had an estimated crystallite size of 18 nm. When used in a catalyst preparation similar to that of Example 1, this material generated 82% conversion. When used in a similar catalyst preparation, except at a reaction temperature of about 80° C., the conversion was 64% after 2 hours.

Example 22

This Example 22 shows that the spray drier product may be fed continuously to a thermal processor and that low pressure in the thermal processor is not required to obtain satisfactory results.

The procedure in Example 21 was repeated, except that the $NiCl_2$ dihydrate isolated from the spray dryer was then fed continuously into a thermal processor that was heated indirectly by a hot oil supply at 244° C., resulting in the bulk temperature being about 10° C. lower. The pressure in the thermal processor was maintained slightly below atmospheric. The anhydrous product discharged from the thermal processor contained a residual moisture of less than 1 weight percent $H_2O$. When used in a catalyst preparation similar to that of Example 1, except at a reaction temperature of about 80° C., this material generated 62% conversion.

What is claimed:

1. A process for preparing a hydrocyanation catalyst comprising contacting at least one bidentate phosphorus-containing ligand selected from the group consisting of bidentate phosphites, bidentate phosphinites, and bidentate phosphines with nickel chloride in the presence of a nitrile solvent and a reducing metal which is more electropositive than nickel, the nickel chloride being in molar excess with respect to the reducing metal in a molar ratio of 1.1:1 to 100:1.

2. The process of claim 1 wherein the reducing metal is selected from the group consisting of Na, Li, K, Mg, Ca, Ba, Sr, Ti, V, Fe, Co, Cu, Zn, Cd, Al, Ga, In, and Sn.

3. The process of claim 2 further comprising separating unreacted nickel chloride from the hydrocyanation catalyst.

4. The process of claim 2 where the reducing metal is Zn or Fe.

5. The process of claim 4 wherein the catalyst preparation is conducted at a temperature of 30 to 100° C. and at a pressure of 5 to 50 psia (34 to 340 kPa).

6. The process of claim 5 wherein the catalyst preparation is conducted at a temperature of 50 to 90° C.

7. The process of claim 6 wherein the molar ratio of nickel chloride to reducing metal is 2:1 to 50:1.

8. The process of claim 7 wherein the molar ratio of nickel chloride to reducing metal is 2:1 to 25:1.

9. The process of claim 8 wherein the bidentate phosphorous-containing ligand is a compound selected from the group consisting of:

$$(R^1O)_2P(OZO)P(OR^1)_2,$$

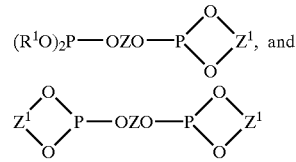

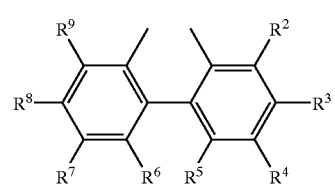

wherein:

$R^1$ is phenyl or naphthyl, wherein the phenyl or naphthyl is unsubstituted or substituted with one or more $C_1$ to $C_{12}$ alkyl or $C_1$ to $C_{12}$ alkoxy groups; and Z and $Z^1$ are independently selected from the group consisting of radicals having the formula I,II,III and IV:

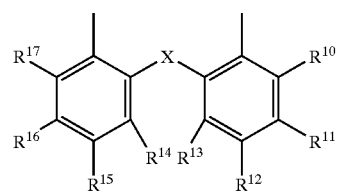

wherein:

$R^2$ and $R^9$ are the same and are H, $C_1$ to $C_{12}$ alkyl, or $C_1$ to $C_{12}$ alkoxy;

$R^3$ and $R^8$ are the same and are H, $C_1$ to $C_{12}$ alkyl, or $C_1$ to $C_{12}$ alkoxy;

$R^4$ and $R^7$ are the same and are H, $C_1$ to $C_{12}$ alkyl, or $C_1$ to $C_{12}$ alkoxy;

$R^5$ and $R^6$ are the same and are H, $C_1$ to $C_{12}$ alkyl, or $C_1$ to $C_{12}$ alkoxy;

II wherein:

X is O, S, or $CH(R^{18})$;

$R^{10}$ and $R^{17}$ are the same and are H, $C_1$ to $C_{12}$ alkyl, or $C_1$ to $C_{12}$ alkoxy;

$R^{11}$ and $R^{16}$ are the same and are H, $C_1$ to $C_{12}$ alkyl, or $C_1$ to $C_{12}$ alkoxy;

$R^{12}$ and $R^{15}$ are the same and are H, $C_1$ to $C_{12}$ alkyl, or $C_1$ to $C_{12}$ alkoxy; $R^{13}$ and $R^{14}$ are the same and are H, $C_1$ to $C_{12}$ alkyl, or $C_1$ to $C_{12}$ alkoxy; and $R^{18}$ is H or $C_1$ to $C_{12}$ alkyl;

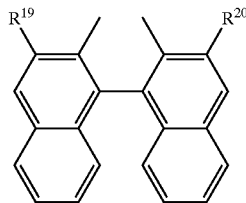

III wherein:
$R_{19}$ and $R_{20}$ are the same and are H or $CO_2R^{21}$; and
$R^{21}$ is $C_1$ to $C_{12}$ alkyl or $C_6$ to $C_{10}$ aryl, unsubstituted or substituted with $C_1$ to $C_4$ alkyl groups;

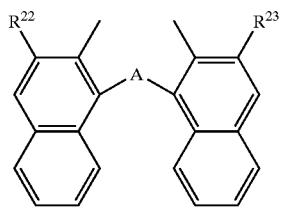

IV wherein:
A is O, S, CH($R^{24}$);
$R^{22}$ and $R^{23}$ are the same and are H or $CO_2R^{25}$;
$R^{24}$ is H or $C_1$ to $C_{12}$ alkyl; and
$R^{25}$ is $C_1$ to $C_{12}$ alkyl.

10. The process of claim 9 wherein unreacted nickel chloride is separated from the hydrocyanation catalyst and is recycled for use in the hydrocyanation catalyst production process.

11. The process of claim 9 wherein the nickel chloride initially contacted with the nitrile solvent and bidentate phosphorous-containing ligand comprises anhydrous nickel chloride.

12. The process of claim 11 wherein the anhydrous nickel chloride is produced by a process comprising treating hydrated nickel chloride at a temperature of about 200 to about 240° C. for a time less than 12 hours.

13. The process of claim 12 wherein the hydrated nickel chloride is $NiCl_2 \cdot 6H_2O$ or $NiCl_2 \cdot 2H_2O$.

14. The process of claim 11 wherein the anhydrous nickel chloride is produced by a process comprising:
  (a) spray drying an aqueous solution of nickel chloride at an exit temperature of about 120 to about 150° C.; and
  (b) thermally drying the product of step (a) at a temperature between about 200 to about 240° C. for a time of less than 12 hours.

15. The process of claim 14 wherein the spray drying cut temperature is about 130 to about 135° C. with a mean residual time of heat exposure between 1 and 45 seconds.

16. The process of claim 15 wherein the reducing metal has a particle size of 20 mesh or less.

17. The process of claim 1 wherein the nitrile solvent is an unsaturated nitrile.

18. The process of claim 17 wherein the nitrile solvent is selected from the group consisting of 3-pentenenitrile and 2-methyl-butenenitrile.

* * * * *